United States Patent [19]

Lawter et al.

[11] Patent Number: 5,500,228
[45] Date of Patent: * Mar. 19, 1996

[54] PHASE SEPARATION-MICROENCAPSULATED PHARMACEUTICALS COMPOSITIONS USEFUL FOR ALLEVIATING DENTAL DISEASE

[75] Inventors: James R. Lawter, Goshen; Michael G. Lanzilotti, Pearl River, both of N.Y.

[73] Assignee: American Cyanamid Company, Madison, N.J.

[*] Notice: The portion of the term of this patent subsequent to Mar. 19, 2008, has been disclaimed.

[21] Appl. No.: 617,382

[22] Filed: Nov. 26, 1990

Related U.S. Application Data

[63] Continuation of Ser. No. 288,739, Dec. 22, 1988, abandoned, which is a continuation-in-part of Ser. No. 54,372, May 26, 1987, Pat. No. 5,000,886.

[51] Int. Cl.⁶ .............................. A61K 6/00; A61K 9/14; A61K 9/50; A61K 47/30
[52] U.S. Cl. .................... 424/486; 424/426; 424/435; 514/900; 514/902
[58] Field of Search ................. 424/78, 426, 435, 424/425, 460, 78.07, 486; 514/899, 900, 902

[56] References Cited

U.S. PATENT DOCUMENTS

| | | | |
|---|---|---|---|
| 3,887,699 | 6/1975 | Yolles | 424/78 |
| 3,972,995 | 8/1976 | Tsuk et al. | 424/435 |
| 4,039,653 | 8/1977 | DeFoney et al. | 424/435 |
| 4,059,686 | 11/1977 | Tanaka et al. | 424/435 |
| 4,226,848 | 10/1980 | Nagai et al. | 514/772.1 |
| 4,250,163 | 2/1981 | Nagai et al. | 514/772.1 |
| 4,369,172 | 1/1983 | Schor et al. | 424/468 |
| 4,434,153 | 2/1984 | Urquhart et al. | 424/469 |
| 4,568,535 | 2/1986 | Loesche | 424/435 |
| 4,568,536 | 2/1986 | Kronenthal et al. | 424/435 |
| 4,569,837 | 2/1986 | Suzuki et al. | 514/772.2 |
| 4,585,651 | 4/1986 | Beck et al. | 424/196.11 |
| 4,597,960 | 7/1986 | Cohen | 424/435 |
| 4,622,244 | 11/1986 | Lapka et al. | 424/497 |
| 4,650,665 | 3/1987 | Kronenthal et al. | 424/435 |
| 4,652,441 | 3/1987 | Okada et al. | 424/497 |
| 4,675,189 | 6/1987 | Kent et al. | 424/426 |
| 4,685,883 | 8/1987 | Jernberg | 604/890 |
| 4,764,377 | 8/1988 | Goodson | 424/449 |
| 4,780,320 | 10/1988 | Baker | 424/493 |

Primary Examiner—Jeffrey E. Russel
Attorney, Agent, or Firm—Hedman, Gibson & Costigan

[57] ABSTRACT

Oral compositions for the local administration of a therapeutic agent to a periodontal pocket of a patient for alleviating dental disease comprise a plurality of dry, discrete microparticles each of which comprise an effective amount of at least one therapeutic agent dispersed in a matrix comprising a biocompatible and biodegradable polymer of preferably, the dry microparticles and dispersed into the periodontal pocket whereby upon contact with the moist environment of the pocket, they hydrate, become tacky and adhere to one another and to the tissues surrounding the pocket so as to maintain intimate contact with the involved tissue so as to induce long term therapeutic benefits.

7 Claims, 6 Drawing Sheets

PHASE SEPARATION-MICROENCAPSULATED PHARMACEUTICALS COMPOSITIONS USEFUL FOR ALLEVIATING DENTAL DISEASE

This application is a continuation of Ser. No. 07/288,739, filed Dec. 22, 1988, now abandoned, which is a continuation in part of Ser. No. 07/054,372, filed May 26, 1987 which is now U.S. Pat. No. 5,000,886. This application is related to Ser. No. 07/593,125, filed Oct. 5, 1990 which is now U.S. Pat. No. 5,236,355; Ser. No. 07/289,076, filed Dec. 22, 1988, now abandoned; and Ser. No. 07/602,414, filed Oct. 22, 1990 which is now U.S. Pat. No. 5,143,661.

This invention is concerned with pharmaceutical compositions comprising therapeutic agent-containing microparticles produced by phase separation microencapsulation. More particularly, the microparticles, which comprise an effective amount of at least one therapeutic agent dispersed in a biocompatible and biodegradable polymer, provide especially effective treatment for dental diseases, e.g., periodontitis.

BACKGROUND OF THE INVENTION

Improved methods for providing compositions for controlled release of therapeutic agents are disclosed and exemplified in applicants' above-mentioned parent application Serial No. 07/054,372, now U.S. Pat. No. 5,000,886. It has now been discovered that such novel compositions are uniquely suitable for treating dental diseases.

Drugs are conventionally administered orally or via injection, often at a site remote from the target. Over a relatively short period of time, the drug diffuses into the circulatory system of the patient and is distributed to the various organs and tissues, at least one of which is the intended target for the drug. The action of the drug on organs other than the target may result in undesirable side effects. Finally, the drug is metabolized or otherwise reversibly removed from the organism by excretion or chemical deactivation. When drugs are delivered orally or by injection by conventional, non-sustained release formulations the level and duration of availability of the drug cannot be controlled independently; only the size and frequency of the dose can be manipulated. Typically, there is an initially high concentration of available drug at the site of injection or in the circulatory system which then decreases gradually as the drug is distributed and consumed within the body of the patient.

In controlled or sustained delivery, a formulation of drug and a carrier is generally administered to the patient by ingestion or implantation. The carrier forms a drug reservoir that protects the stored drug from extraneous removal mechanisms and releases the drug to the biological reservoir at a predetermined rate. Controlled, sustained delivery of a drug prevents undesirable peaking of blood levels and makes the drug available at an optimum and substantially uniform concentration over an extended period of time. Only the released drug is subject to removal via metabolism and excretion. In the controlled sustained delivery method, there is potential for control of the drug release rate by factors inherent in the delivery package itself. Some of these inherent factors, such as the rate of hydrolysis of an absorbable polymer, or the rate of transdermal diffusion are in contrast to the externalized controls associated with classical delivery methods, e.g., rate of tablet intake, frequency of injections, etc. In accordance with prior methods, the maintanance of therapeutic blood levels of an antibiotic, for example, requires a fairly precise dosing of tablets. Though this may be uncomplicated for many adults, it may be difficult where gastric problems are present or for infants, the very infirm, or in veterinary work, such as with range animals.

The present invention provides a therapeutic composition which releases and maintains effective and predictable drug levels, thus eliminating the need for continual external supervision.

Known methods for controlled release of drugs to treat dental disease include the antibiotic-containing fibers described in Goodson, U.S. Pat. No. 4,175,326. The fibers are difficult to pack into the periodontal pocket and contact with the involved tissues may not be complete.

Baker, European Patent Application No. 0,244,118, describes therapeutic agent-containing microparticles suspended in a liquid carrier, but when placed into the periodontal pocket they wash out, and do not swell or stick to the involved tissues.

The dry microparticles of the present invention comprise a core material surrounded by a coating or encapsulating substance which is normally a polymer. Upon contact with moisture, these become tacky and adhere to the involved tissue and provide long term therapeutic effectiveness. Microparticles may consist of one or more core particles surrounded by a coating, or the microencapsulated substance may exist as one or more irregularly shaped particles surrounded by a coating which may have spherical form, or the exterior of the microparticles may be irregular in shape. The aspect ratio of the microparticles should be less than about 3.

In general, microparticles are produced to provide protection for the core material and/or to control the rate of release of the core material to the surrounding environment. Also included within the term "microparticles" are those in which the pharmaceutical agent is present as a solid solution in the coating, and may be present at one or more points or portions of the surface of the microparticles. The terms microcapsules and microspheres have also been applied to the above-named microparticles.

As suggested by Beck et al., U.S. Pat. No. 4,585,651, which discloses pharmaceutical compositions comprising microparticles of a pharmaceutical agent incorporated in a biocompatible and biodegradable matrix material, the methods for preparation of microparticles may be classified in three principal types:

(1) phase separation methods including aqueous and organic phase separation processes, melt dispersion and spray drying;

(2) interfacial reactions including interfacial polymerization, in situ polymerization and chemical vapor depositions; and (3) physical methods, including fluidized bed spray coating, electrostatic coating and physical vapor deposition. The preferred method for this invention is (1).

Kent et al., European Patent Publication Number 052,510 disclose the microencapsulation of water soluble polypeptides in biocompatible, biodegradable polymers such as Poly(lactide-co-dl-glycolide)copolymers, also by a phase separation process utilizing an alkane solvent, and specifically exemplifies heptane as a hardening solvent.

The prior art hardening agents including hexane, heptane, cyclohexane and other alkane solvents leave substantial amounts of hardening agent residues in the microparticles. Tests have shown that heptane hardened microparticles typically contain 5–15% by weight of heptane. Since hardening agents can ultimately be released, low toxicity is of paramount importance for hardening agents used to produce microparticles for pharmaceutical applications, and it would be advantageous to provide the same.

In addition, a further drawback in use of hydrocarbon hardening agents of the prior art is that they are flammable and therefore require the use of explosion-proof facilities for manufacturing microparticles.

In the above-mentioned patent application Ser. No. 07/054,372, now U.S. Pat. No. 5,000,886, it is discloser that if volatile silicone fluids are used as hardening agents, the drawbacks of the prior art are overcome because of their very low toxicity and non-flammability characteristics. Microparticles produced by the phase separation microencapsulation process are different and better than those of the prior art because the residual hardening agent content is very low, e.g., on the order of less than 3 wt. %, preferably less than 1 wt. %. The results obtained therein were surprising because, while the coating material solvent is readily removable by vacuum drying, it had been the experience that residual prior art hardening agents, once incorporated into microparticles, are not readily removed by drying because they are, by nature, not soluble in the coating material and therefore do not permeate through the coating material.

Volatile silicone fluids are unique because these fluids essentially are not incorporated into the microparticles during the hardening step.

Despite the existence of the above-described sustained release compositions, a need still exists for a biodegradable sustained release composition which is capable of delivering a therapeutic agent for a period of time sufficient to treat a periodontal infection. Such a need is met now by providing dry, discrete microparticles having a hardening agent content of less than about 3% by weight and administering them directly to the periodontal pocket(s) of patients in need of treatment.

DESCRIPTION OF THE DRAWINGS

The invention may be more readily understood by reference to the drawings in which.

SUMMARY OF THE INVENTION

Figure 1:
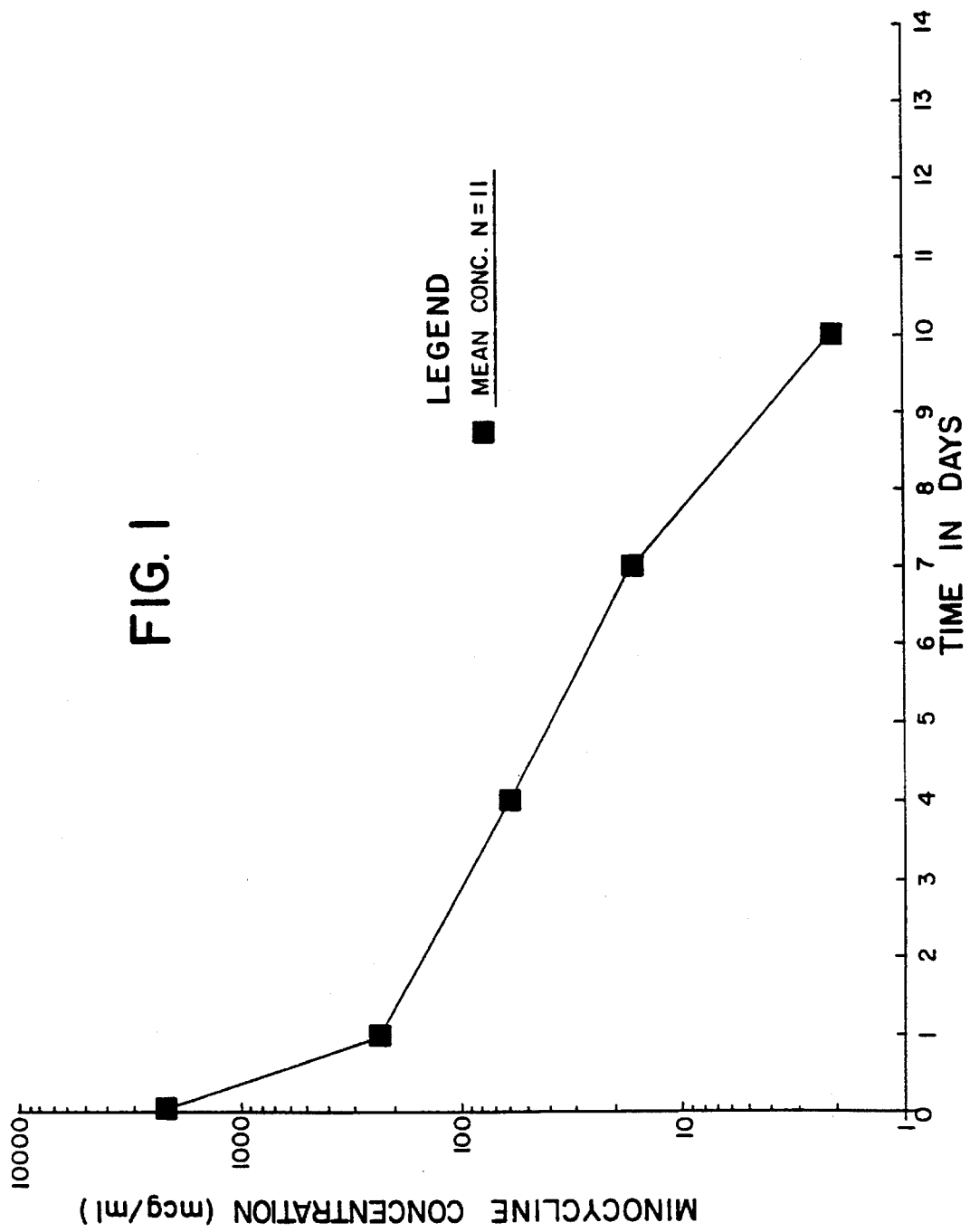
FIG. 1 is a graph illustrating minocycline concentration in crevicular fluid after administration and release from microparticles of Example 1 of this invention over a 10-day period.
Figure 2:
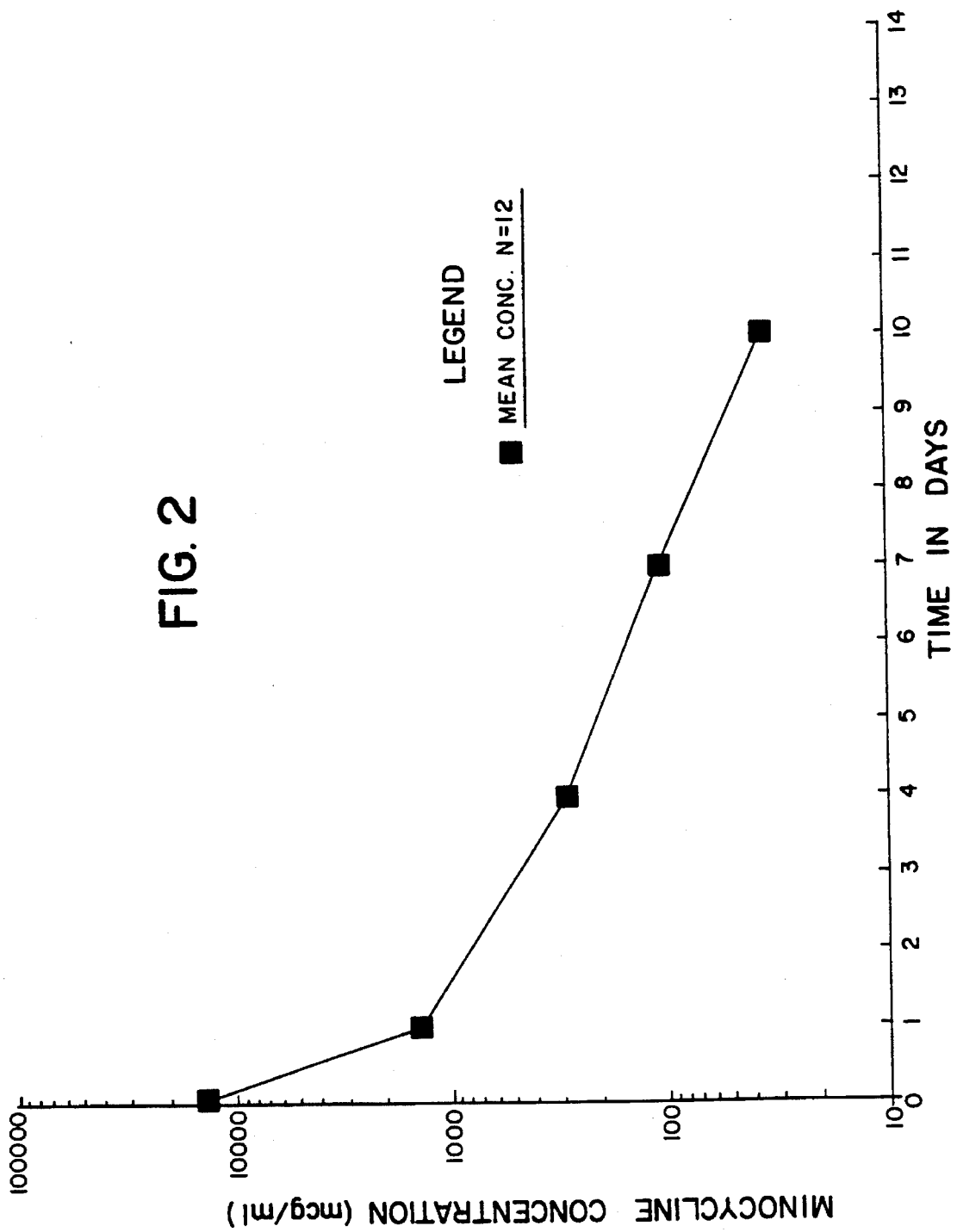
FIG. 2 is a graph illustrating minocycline concentration in crevicular fluid after administration and release from microparticles of Example 2 of this invention over a 10-day period.
Figure 3:
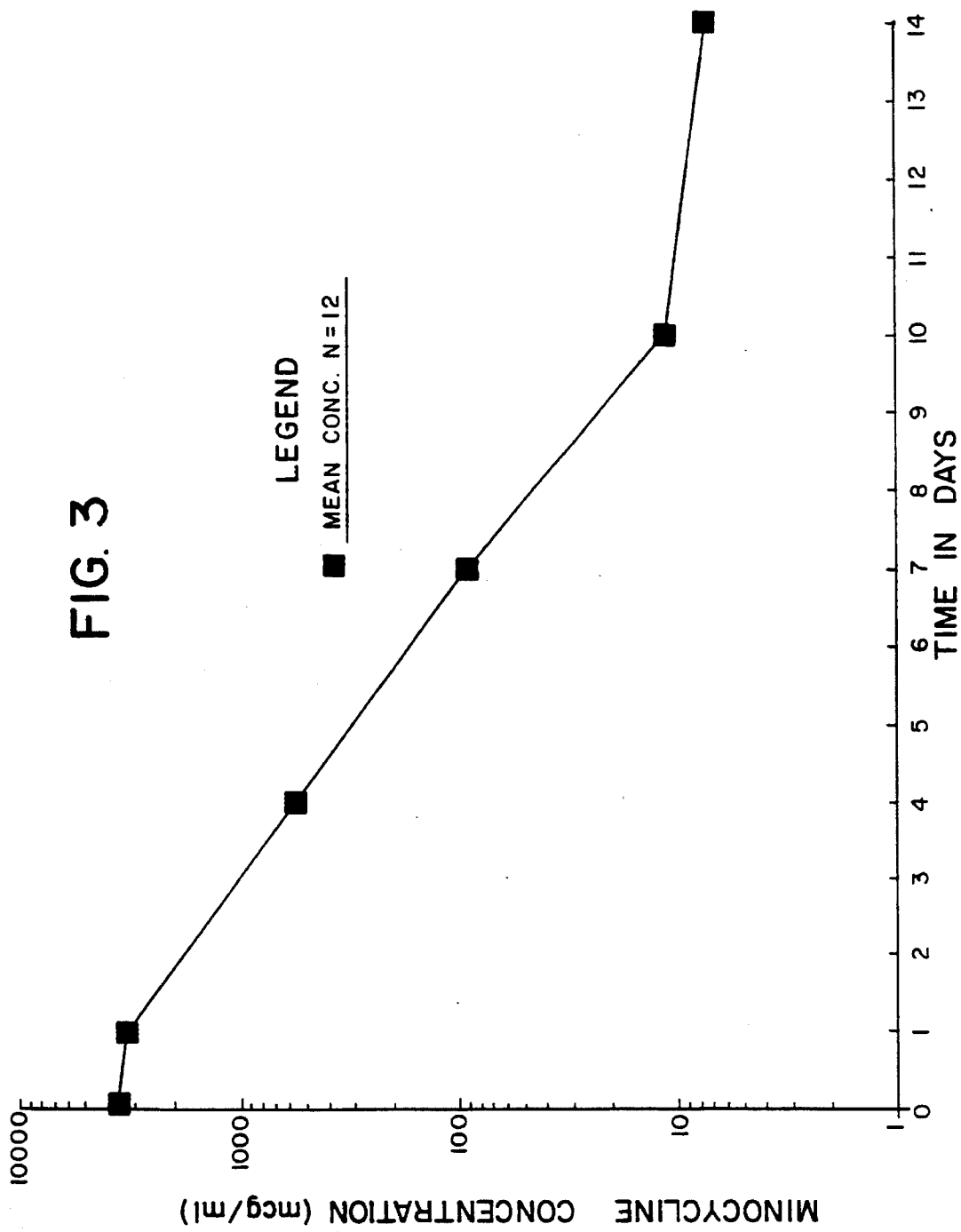
FIG. 3 is a graph illustrating minocycline concentration in crevicular fluid after administration and release from microparticles of Example 3 of this invention over a 14-day period.
Figure 4:
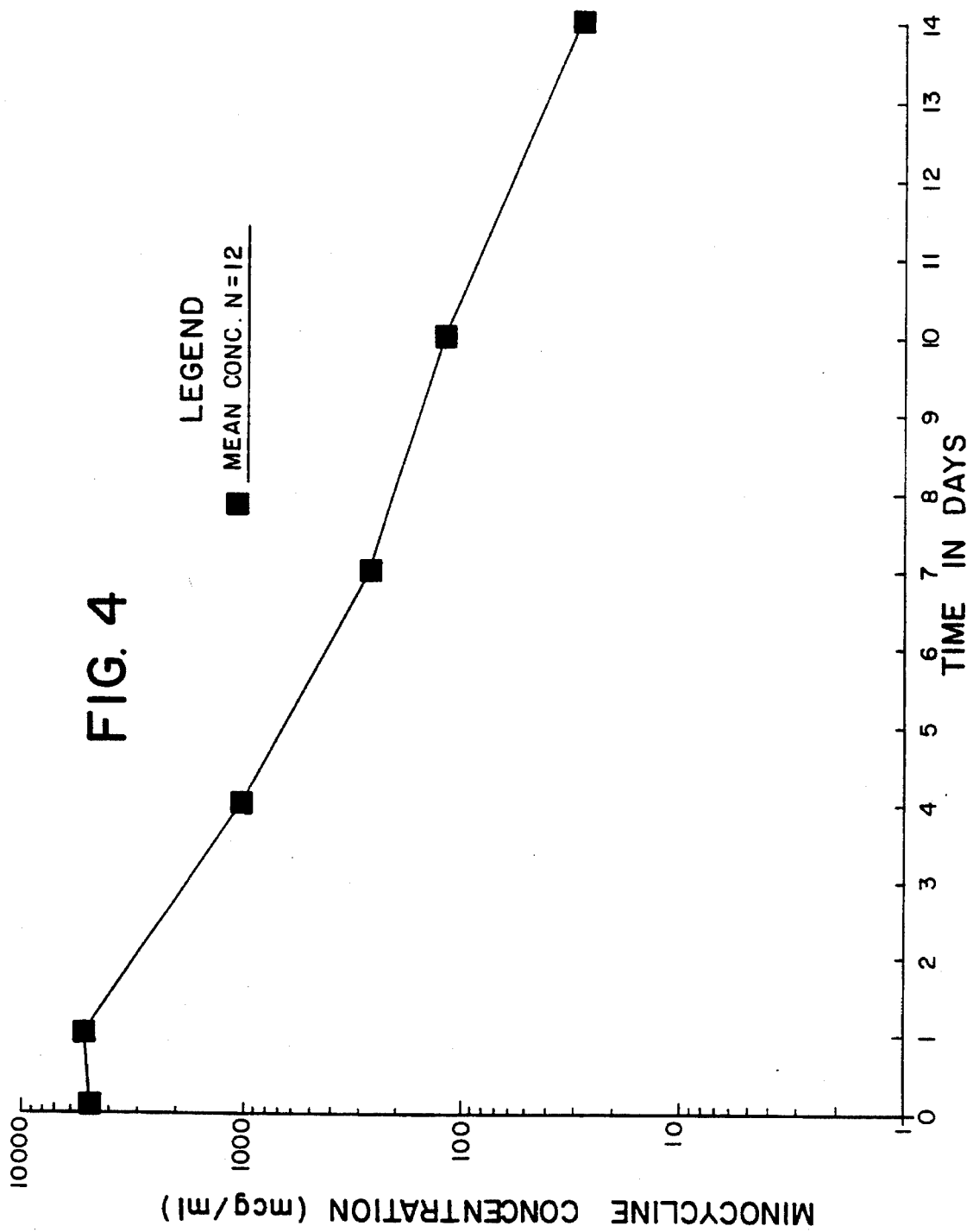
FIG. 4 is a graph illustrating minocycline concentration in crevicular fluid after administration and release from microparticles of Example 4 of this invention over a 14-day period.

In accordance with the present invention, there are provided therapeutic agent-containing microparticles for alleviating dental diseases, which comprise:

(i) an effective amount of at least one therapeutic agent dispersed in (ii) a matrix comprising a biocompatible and biodegradable polymer, said microparticles having been prepared by phase separation microencapsulation, and having a residual hardening agent content of less then about 3% by weight. Such compositions are different from those of the prior art because they have a residual hardening agent content of less than about 3% by weight, preferably less than 1% by weight, and are substantially free of any alkane hardening agents. Typical prior art particles contain 7 weight percent and more of residual hardening agents.

Criteria which core materials must satisfy in order to be microencapsulated by the process of this invention are as follows. The core material must have low solubility in the preferred volatile silicone hardening agent. Low solubility means less than about 5% weight/weight; preferably less than about 1%, and most preferably less than about 0.1%. Also in the case of core materials which are microencapsulated as solids or liquids dispersed in the coating solution, the concentrated coating solution phase generated upon addition of the non-solvent must wet the core phase in preference to the continuous phase. In the case of the core materials which are soluble in the initial coating solution, the core material must partition into the coating phase generated upon addition of the coating non-solvent. Thus, the class of core materials which may be microencapsulated by the process of this invention is determined by the physicochemical properties of the core, coating, coating solvent and hardening agent.

DETAILED DESCRIPTION OF THE INVENTION

The present invention provides a core material surrounded by a coating or encapsulating substance which is normally a polymer. Among the encapsulating polymers which can be utilized, there are named: polyglycolide, polylactide (L OR DL), poly(glycolide-co-l-lactide), poly(glycolide-co-dl-lactide), poly(p-dioxanone), poly(glycolide-co-triethylene carbonate), a block copolymer of polyglycolide, trimethylene carbonate and polyethylene oxide, poly(alkylene diglycolates), poly(alkylene succinates), poly(alkylene oxalates), poly(caprolactone), poly(alpha-hydroxybutyric acid), poly(ortho esters), poly(anhydrides), poly(amide esters), poly(alkylene tartrate), and poly(alkylene fumarate).

In addition, blends of the above polymers and other copolymers of the above may be used.

The preferred encapsulating polymer poly(glycolide-lactide) is similar in structure to the absorbable suture materials, which have been marketed for many years.

The choice of non-solvent is dicatated by the chemical nature of the encapsulation polymer and the polymer solvent. The non-solvent must be miscible with the polymer solvent and, as the name implies, a non-solvent for the encapsulating polymer or coating. The non-solvent must have greater affinity for the polymer solvent than the encapsulating polymer. Typical non-solvents are silicone oils (polydimethylsiloxane), vegetable oils, polyisobutylene, mineral oils, cyclic polydimethylsiloxanes and related oils and the like.

Encapsulating polymers or coating solvents must be miscible with the hardening agent which in the process of this invention is a volatile silicone fluid. Typically, halogenated organic solvents such as methylene chloride and 1,1,2 trichloroethane or other $C_1$–$C_4$ halogenated alkanes are employed. Other useful solvents, includes ethylacelate, methyl acetate, ethyl formate and methyl formate.

The volatile silicone fluid is preferably octamethylcyclotetrasiloxane or decamethylcyclopentasiloxane or a low molecular weight linear polydimethylsiloxane, such as hexamethyldisiloxane. These are commercially available. Preferrred is Dow Corning's Silicone Fluid 244 which is comprised of octamethylcyclotetrasiloxane.

The microparticle formulation provides significant advances over other formulations designed for the treatment of periodontal disease. The inactive ingredient is biodegradable so that it is not necessary to remove the formulation from the pocket after the drug has been released. Further, the quantity of polymer present in the periodontal pocket is so small and the degradation rate sufficiently slow that the quantity of acid produced does not adversely affect the pocket tissues.

The periodontal microcapsules of this invention are prepared by a phase separation microencapsulation which most conveniently comprises:

(1) dispersion of the milled solid active ingredient, typically less than 20 microns in diameter, in a solution of the encapsulating polymer, e.g. poly(glycolide-co-dl-lactide);

(2) addition of a phase inducer to the suspension to cause the polymer to separate out (coacervate) in the form of small solvent-polymer droplets which adhere to the therapeutic agent phase;

(3) addition of the above mixture to a hardening solvent which extracts the polymer solvent from the dispersed solvent-polymer-therapeutic agent phase to yield solid microparticles;

(4) recovery of the therapeutic agent-containing microparticles by filtration of the suspension through a screen; and (5) drying the periodontal microparticles such as by vacuum drying.

The methods and materials used to prepare microencapsulated pharmaceutical agents are well known to those skilled in the art as evidenced by the above-mentioned patents and publications.

The composition of the copolymer is preferably selected so as to degrade within a period of about one month or less, and also so that it rapidly hydrates upon administration to the moist environment of the crevicular pocket. Hydration causes the polymer to become tacky so that the microparticles adhere to one another and to the tissues surrounding the pocket. Adhesion to the tissues surrounding the pocket provides a means for retention of the formulation in the pocket and permits delivery of the therapeutic agent over periods of up to two weeks, or longer. Adhesion is necessary to prevent expulsion of the dosage form from the periodontal pocket by crevicular fluid which continuously flows from the pocket.

The microparticles may range in diameter from about 0.1 to 1000 microns, preferably about 10 to about 200 microns and especially preferably 30 to 120 microns, depending on the procedure employed. They may be administered to a subject by any suitable means or route desired. The amount of pharmaceutical agent used will comprise an effective amount, which may range down to as low as 0.00001% by weight, or lower, for certain hormones, e.g., tissue growth factors. If an antibiotic is used, the amount will usually comprise from about 1% to about 50% by weight of the microparticles, preferably from about 5 to about 40% by weight of the microparticles, and especially preferably from 20 to 30% by weight of the microparticles.

While the composition of matter employing the above described hardening agents and the process by which the microparticles are produced are generally applicable to a variety of pharmaceutical agents, they are specifically applicable to therapeutic agents containing microparticles such as those listed below.

Among the pharmaceutical agents for dental treatment which can be used in general are: antibacterial agents, antifungal agents, antibiotic agents, anti-inflammatory agents, dentinal desensitizers, odor masking agents, immune reagents, anesthetic agents, antiseptic agents, nutritional agents, antioxidants, lipopolysaccharide complexing agents, peroxides, tissue growth factors or a mixture of any of the foregoing. Although broadly applicable to therapeutic agents described above, preferred are tetracycline compounds in general, and special mention for purposes of this invention is made of the use of members of the tetracycline family comprising substituted 4-, 7-, and 9-aminotetracyclines which may be represented by the following general formula:

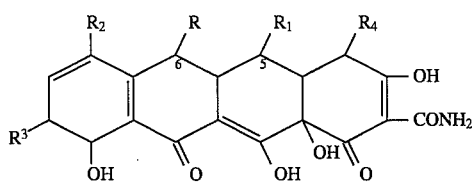

where R is hydrogen or methyl, $R_1$ is hydrogen or hydroxyl, and $R_2$, $R_3$ and $R_4$ are hydrogen, mono(lower alkyl)amino or di(lower alkyl) amino with the proviso that $R_2$, $R_3$ and $R_4$ cannot all be hydrogen. Typical compounds represented by the above general formula are, for example, 7-methylamino-6-deoxy-6-demethyltetracycline, 7-ethylamino-6-deoxy-6-demethyltetracycline, 7-isopropylamino-6-deoxy-6-demethyltetracycline, 9-methylamino-6-deoxy-6-demethyltetracycline, 9-ethylamino-6-deoxy-6-demethyltetracycline, 9-isopropylamino-6-deoxy-6-demethyltetracycline, 7,9-di(ethylamino)-6-deoxy-6-demethyltetracycline, 7-dimethylamino-6-deoxy-6-demethyltetracycline, 9-dimethylamino-6-deoxy-6-demethyltetracycline, -methylamino-6-deoxytetracycline, 9-ethylamino-6-deoxytetracycline, 7,9-di(methylamino)-6-deoxytetracycline, 7-diethylamino-6-deoxytetracycline, 9-diethylamino-6-deoxytetracycline, 7,9-di(methylethylamino)-6-deoxytetracycline, 7-methylamino-9-ethylamino-6-deoxytetracycline, and 9-methylamino-5-hydroxy-6-deoxytetracycline.

Preferred members of this family comprise tetracycline compounds selected from (a) 7-dimethylamino-6-deoxy-6-demethyltetracycline;

(b) 7-methylamino-6-deoxy-6-demethyltetracycline;

(c) 9-methylamino-6-deoxy-6-demethyltetracycline;

(d) 7-ethylamino-6-deoxy-6-demethyltetracycline;

(e) 7-isopropylamino-6-deoxy-6-demthyltetracycline;

(f) 6-deoxy-5-oxytetracycline (g) a non-toxic acid addition salt or hydrate of (a)–(f), inclusive or (h) a mixture of any of the foregoing.

Special mention is made of the tetracycline compounds, 7-dimethylamino-6-deoxy-6-demethyltetracycline, 6-deoxy-5-oxytetracycline and their non-toxic acid addition salts or hydrates, e.g., hydrochloric, sulfonic, trichloroacetic acid salts, and the like, especially preferably the hydrochloric acid addition salts. The first named compound in the form of its monohydrochloride is also known as minocycline hydrochloride and the second compound is also known in the form of its monohydrate as doxycycline hyclate. These compounds and methods for their preparation are disclosed in U.S. Pat. Nos. 3,148,212, 3,200,149 and 3,226,436.

Minocycline is a potent semisynthetic tetracycline analog with activity against a wide range of gram-positive and gram-negative organisms. It has been shown to concentrate in human periodontal fluid at levels five times higher than serum levels and has proven effective against oral microorganisms while producing an improvement in gingival health. When inserted in microencapsulated form directly into the infected gingival site of beagle dogs, minimum inhibitory concentrations (MIC's) can be achieved for periods up to two weeks. When compared with existing dosage forms needed to attain similar periodontal pocket fluid levels, administration of minocycline periodontal powder requires a dose served hundred fold less than systemic formulations.

Accordingly, by using the composition of the present invention for treating periodontal diseases, side effects due to oral administration of a tetracycline, minocycline, doxycycline, and the like, such as those of the digestive system, for example, anorexia, nausea and diarrhea, biochemical abnormalities such as thrombocytopenia and eosinophilia or bacterial change can be reduced and, thereby, the composition is useful from the clinical point of view.

Thus, in a preferred aspect, the present invention provides for alleviating periodontal diseases which comprises applying the above composition containing a tetracycline such as minocycline, doxycycline, and the like to the inside of periodontal pockets.

The sterile therapeutic agent-containing periodontal powder is administered by any convenient procedure. As is described in the related co-pending application, it is preferred to package and administer it with a specially designed dispenser, which is enclosed in a moisture tight aluminum foil pouch. The dispenser, shown in FIG. 6 to be a syringe-type instrument comprised of polypropylene or polyethylene resin, delivers a single dose, which, for example, contains about 1 mg of minocycline. The dosage form is sterilized by gamma radiation after being packaged in the foil laminated pouch.

The formulation is administered as a dry powder, which absorbs water upon contact with the moist environment of the periodontal pocket. Crevicular fluid causes the microparticles to become tacky and to adhere to one another and to the pocket tissues. Absorption of water from the crevicular fluid also triggers releases of the active ingredient. It is hypothesized that upon absorption of water, the therapeutic agent dissolves and increases in volume. This causes the formation of channels in the microparticles, through which the drug may diffuse. During and following release of the drug, the polymer degrades or dissolves to produce small molecular weight fragments, which may be transported systemically from the pocket by the crevicular fluid or by the blood.

The preferred polymeric carrier, poly(glycolide-co-dl-lactide), which serves as a sustained-release delivery system for the new periodontal formulation belongs to a class of polymers known as thermoplastic polyesters. These polymers undergo biodegradation through a process whereby their ester bonds are hydrolyzed to form normal metabolic compounds, lactic acid and glycolic acid.

Copolymers consisting of various ratios of lactic and glycolic acids have been studied for differences in rates of degradation. It has been found that the biodegradation rate depends on the ratio of lactic acid to glycolic acid in the copolymer, and the 50:50 copolymer degrades most rapidly.

A pharmacokinetic investigation of the minocycline periodontal formulations of the present invention was undertaken to produce a dosage form that could be administered to the periodontal pocket and that would yield minocycline concentrations exceeding the Minimum Inhibitory Concentrations (MIC's) (0.05–1.56 mcg/ml) for organisms associated with periodontal disease for a period of up to 14 days. Therefore, a study to evaluate four different minocyline periodontal formulations relative to determining minocyline levels in crevicular fluid was conducted in vivo in a dog model.

The study utilized beagle dogs with surgically created "chronic" intrabony periodontal defects. This model entails the extraction of the two lower fourth premolars and the induction of surgically created intrabony defects at the mesial surface of the first molars and distal surface of the third premolars. Facial, lingual, interproximal bone and denuded (root planed) root surfaces comprise the surgically induced circumference of a 6–7 mm deep intrabony defect.

In sequence, the defects were created as follows: First, the lower fourth premolars were extracted, sockets were allowed to heal for one month, and dogs received a full mouth scaling and tooth cleaning. A mucoperiosteal periondontal flap procedure was then performed in each of the lower quadrants, and intrabony defects were created at the mesial surface of the first molars and distal surface of the third premolars. The bone immediately adjacent to the interproximal surfaces of the the teeth was removed by a dental high-speed drill under constant water irrigation. The cementum lining of the tooth was also removed. Before replacing the periosteal flaps, a stainless steel wire was placed around the neck of the teeth, formed into a loop, and bent into the bony defect, and a piece of aluminum foil, cut to fit the defect, was placed between the wire and the tooth surface. The wires were left in place for six weeks to permit a subgingival plaque to be organized. The wires were then cut and removed, together with the aluminum foil. Dogs were monitored for an additional four weeks.

Figure 6A:
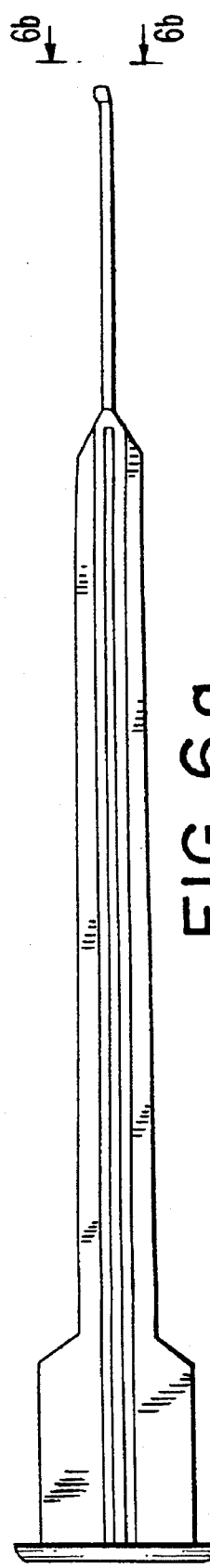
FIG. 6(a-b) illustrates, in longitudinal cross section, a dispensing apparatus for administration of drug microparticles of the therapeutic agent directly to the periodontal cavity in accordance with this invention.
Figure 6B:
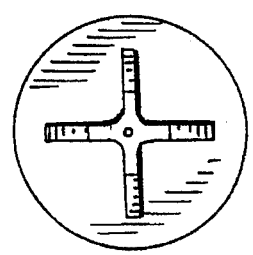

For evaluation of crevicular levels of minocycline, dogs were placed under general anesthesia, and the various formulations were administered into the periodontal pockets associated with the created defects. Formulations were administered in dry form with the aid of a special dispenser (FIG. 6). Visual evaluation (primarily to note physical retention of material) and crevicular fluid collection were performed generally at two and 24 hours and at 4, 7, 10, 14 and 28 days after treatment. Three of the four formulations (A, B, C) were studied for only one treatment administration, while the fourth formulation (D) was studied for two treatment cycles. Samples of gingival fluid were collected on a Periotron paper strip placed at paper strip placed at the orifice of the defect for 30 seconds. The strip was then removed, and the relative amount of fluid was determined by a Periotron 6000 instrument. Paper strips were collected in vials and frozen to −20° C. until assayed.

Strips were assayed for minocycline by a bio-assay technique that involves use of the minocycline-susceptible bacterium *Bacillus cereus*. Bacteria were seeded into nutrient agar. After pouring the agar into petri dishes and allowing the agar to harden, holes were punched into the agar, where the strip specimens were then placed. Plates were then incubated for 16–20 hours at 30° C. Zones of inhibited bacterial growth were plotted, and the quantity of minocycline present was determined by comparison with zones obtained with minocycline solutions of known concentration.

The results are exemplified hereinafter.

Microparticles prepared with a biodegradable encapsulating polymer according to the current invention provide the ideal delivery system for minocycline, doxycycline, and related or similar drugs. Local administration of the microparticles to the periodontal pocket permits the polymer portion of the microparticle to biodegrade and bioerode, resulting in the release of the therapeutic agent into the body for periods ranging from several hours to several weeks.

DESCRIPTION OF THE PREFERRED EMBODIMENTS

The following examples illustrate the invention, but are not intended to limit the claims in any manner whatsover.

EXAMPLE 1

A 5 percent by solution of poly(glycolide-co-dl-lactide) glycolic acid intiated polymer, inherent viscosity, 0.11 dl/g is prepared in methylene chloride. The polymer solution is filtered through a solvent resistant filter having pore openings of 0.2 microns or less. 6.2 grams of milled minocycline hydrochloride is added to 300 g of polymer solution and dispersed with a high shear mixer. This dispersion is tranferred to a microencapsulation vessel comprising a reactor fitted with a propeller-type, variable speed agitator and a valve for draining liquid from the bottom of the vessel. The dispersion is stirred and 300 g of Dow-Corning Silicone 360 medical fluid, 350 centistokes viscosity, is added during about 3 minutes and stirring is continued for about 2 minutes. The dispersion is transferred from the microencapsulation vessel to a hardening tank containing 14 to 20 kg of Dow Corning Silicone 244 fluid. The hardening vessel is equiped with a variable speed, propeller-type agitator. Stirring is carried out for about 2 hours. The microparticle suspension is discharged through a collection screen and the hardening tank is rinsed with about 1 kg of Silicone 244 fluid and discharged through the hardening screen. The combined microparticles are dried under vacuum at a temperature of about 40° C. The dried microparticles of this invention are sieved through a number 80 screen.

EXAMPLE 2-4

The procedure of Example 1 is repeated, substituting three higher molecular weight polymers of the same kind having inherent viscosities, respectively, of 0.22, 0.31 and 0.44. Compositions in accordance with this invention are obtained.

EXAMPLE 5

If the procedure of Example 1 is repeated, substituting for the minocycline hydrochloride an equal weight of doxycycline hyclate, a composition in accordance with this invention is obtained.

EXAMPLE 6-10

Beagle dogs with surgically created "chronic" intrabony periodontal defects are prepared as described above. A dispenser as shown in FIG. 6 is used to administer the compositions of Examples 1–4 in dry form into the periodontal pockets created in the dogs.

Figure 5:
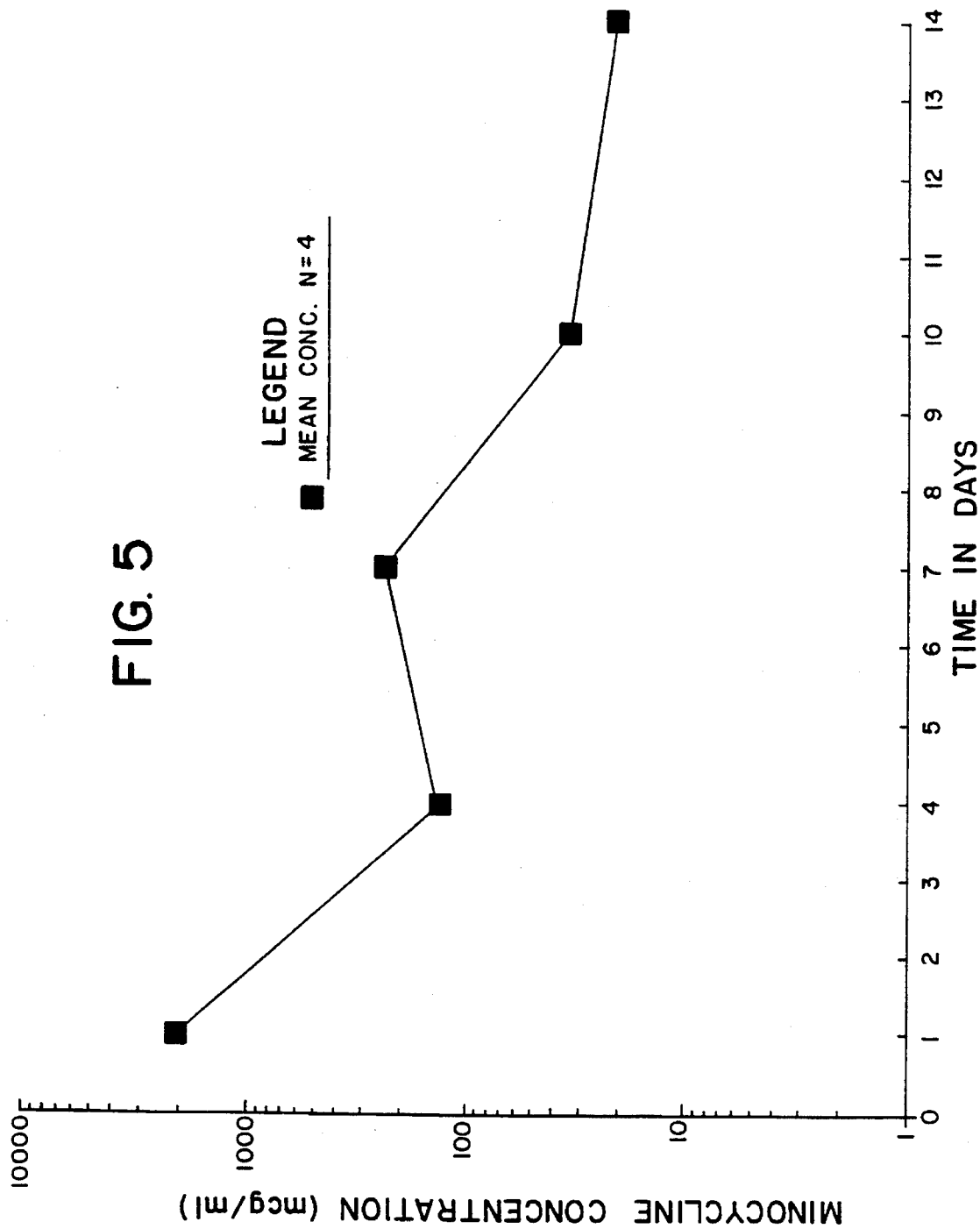
FIG. 5 is a graph illustrating minocycline concentration in crevicular fluid after a second treatment with encapsulated minocycline microparticles of Example 4, as in FIG. 4, showing retention of therapuetic levels over a 14-day period.

Samples of gingival fluid are collected as described above, and analyzed. Visual evaluation and collection of the fluid, are performed at 2 hours, 24 hours, 4 days, 7 days, 10 days, 14 days and 28 days. The dose in all cases corresponded to one milligram of minocycline (free base) per pocket. The strips were assayed for minocycline by microbiological assay with *Bacillus cereus*. The mean crevicular fluid levels of minocycline are plotted versus time in FIGS. 1-5. Example 4 composition was used in a second cycle, FIG. 5. Example 1 maintined mean minocycline levels above 10 mcg/ml for seven days—10 mcg/ml is a therapeutic level. Examples 2 and 3 maintined therapeutic levels for ten days. Example 4 maintained therapeutic levels for fourteen days and maintained such levels for fourteen days on a second cycle.

EXAMPLE 11

If the procedure of Example 6–10 is repeated substituting the doxycycline composition of Example 5, sustained therapeutic levels of doxycycline in the crevicular fluid will be maintained.

The above-mentioned patent, applications and publications are incorporated herein by reference.

Many variations of this invention will occur to those skilled in the art in light of the above, detailed description. For example, instead of minocycline and doxycycline, steroids, non-steroidal anti-inflammatory agents or peptide growth factors can be used. Instead of silicone oil as a non-solvent, mineral oil or peanut oil can be used to make the microparticles. Instead of methylene chloride, other encopsulation polymer solvents such as ethyl acetate, methyl acetate, methyl formate and ethyl formate may be used. Instead of poly(glycolide-co-dl-lactide) other biocompatible, biodegradable polymers which become tacky upon contact with water may be used. All such obvious variations are within the full intended scope of the appended claims.

We claim:

1. Therapeutic agent containing microparticles for alleviating dental disease which comprise:
   (i) an effective amount of at least one therapeutic agent dispersed in
   (ii) a matrix comprising a biocompatible and biodegradable polymer, said microparticles having been made by a phase separation process using a volatile silicone fluid as the sole hardening agent and having a residual volatile silicone fluid content of less than about 3% by weight.

2. The therapeutic agent of claim 1, wherein the volatile silicone fluid is octamethylcyclotetrasiloxane.

3. The therapeutic agent of claim 1, wherein the volatile silicone fluid is decamethylcyclopentasiloxane.

4. The therapeutic agent of claim 1, wherein the volatile silicone fluid is hexamethyldisiloxane.

5. A therapeutic agent as defined in claim 1, wherein the therapeutic agent is an antibiotic.

6. A therapeutic agent as defined in claim 1, wherein the therapeutic agent is minocycline.

7. A therapeutic agent as defined in claim 5, wherein the therapeutic agent is a tetracycline.

* * * * *